(12) United States Patent
Todorokihara

(10) Patent No.: US 8,718,961 B2
(45) Date of Patent: May 6, 2014

(54) FREQUENCY MEASUREMENT METHOD, FREQUENCY MEASUREMENT DEVICE AND APPARATUS EQUIPPED WITH FREQUENCY MEASUREMENT DEVICE

(75) Inventor: Masayoshi Todorokihara, Munich (DE)

(73) Assignee: Seiko Epson Corporation, Tokyo (JP)

( * ) Notice: Subject to any disclaimer, the term of this patent is extended or adjusted under 35 U.S.C. 154(b) by 411 days.

(21) Appl. No.: 12/896,106

(22) Filed: Oct. 1, 2010

(65) Prior Publication Data

US 2011/0082656 A1  Apr. 7, 2011

(30) Foreign Application Priority Data

Oct. 6, 2009  (JP) ................. 2009-232501

(51) Int. Cl.
*G01R 23/165* (2006.01)
*G01R 23/00* (2006.01)
*G01R 23/02* (2006.01)
*G01R 23/167* (2006.01)

(52) U.S. Cl.
USPC ............. 702/78; 702/75; 702/76; 702/83

(58) Field of Classification Search
USPC ........... 702/19, 33, 44, 75, 78, 141, 142, 149, 702/160, 188; 341/118; 370/516; 375/324
See application file for complete search history.

(56) References Cited

U.S. PATENT DOCUMENTS

| | | | |
|---|---|---|---|
| 2,627,033 A | 1/1953 | Jensen et al. | |
| 2,840,812 A | 6/1958 | Di Giacomo | |
| 2,944,219 A | 7/1960 | Isokazu Tanaka et al. | |
| 3,026,473 A | 3/1962 | De Mott | |
| 3,056,085 A | 9/1962 | James et al. | |
| 3,144,623 A | 8/1964 | Steiner | |
| 3,227,952 A | 1/1966 | Proebster et al. | |
| 3,310,660 A | 3/1967 | Cogar | |
| 3,372,346 A | 3/1968 | Rogers et al. | |
| 3,407,290 A | 10/1968 | Atrubin | |
| 3,440,617 A | 4/1969 | Lesti | |
| 3,486,007 A | 12/1969 | Jacobson | |

(Continued)

FOREIGN PATENT DOCUMENTS

CN  1862263 A  11/2006
EP  0 484 629 A2  5/1992

(Continued)

OTHER PUBLICATIONS

U.S. Appl. No. 12/783,900, filed May 20, 2010 in the name of Todorokihara.

(Continued)

*Primary Examiner* — Marc Armand
*Assistant Examiner* — Felix Suarez
(74) *Attorney, Agent, or Firm* — Oliff PLC

(57) ABSTRACT

A frequency measurement device includes: a counter section that counts a supplied pulse stream signal to be measured at a predetermined time interval and outputs a stream of count values corresponding to the frequency of the signal to be measured; and a low-pass filter section that performs a filtering process on the stream of count values, the low-pass filter section including moving average filters in multiple stages, and an output of at least one moving average filter among the moving average filters in multiple stages is downsampled.

7 Claims, 12 Drawing Sheets

(56) References Cited

U.S. PATENT DOCUMENTS

| | | |
|---|---|---|
| 3,551,826 A | 12/1970 | Sepe |
| 3,553,579 A | 1/1971 | Teixeira |
| 3,557,796 A | 1/1971 | Keller et al. |
| 3,605,017 A | 9/1971 | Chertok et al. |
| 3,609,308 A | 9/1971 | Lemon et al. |
| 3,624,494 A | 11/1971 | Turan |
| 3,652,838 A | 3/1972 | Dillon et al. |
| 3,686,565 A | 8/1972 | Kelem et al. |
| 3,697,870 A | 10/1972 | Brenner |
| 3,704,414 A | 11/1972 | Herbst |
| 3,708,686 A | 1/1973 | Butler, Jr. et al. |
| 3,733,471 A | 5/1973 | Gilberg |
| 3,736,510 A | 5/1973 | Wu |
| 3,742,353 A | 6/1973 | Parisi |
| 3,743,940 A | 7/1973 | Yamagata |
| 3,745,380 A | 7/1973 | Kitajima et al. |
| 3,750,014 A | 7/1973 | Gaw |
| 3,755,734 A | 8/1973 | Blanyer |
| 3,761,740 A | 9/1973 | Naïve |
| 3,766,818 A | 10/1973 | Prohofsky |
| 3,775,681 A | 11/1973 | Konrad |
| 3,777,121 A | 12/1973 | Jamieson |
| 3,780,346 A | 12/1973 | Gagnon |
| 3,795,771 A | 3/1974 | Gundersen et al. |
| 3,803,487 A | 4/1974 | Iten |
| 3,812,427 A | 5/1974 | Coulter |
| 3,823,374 A | 7/1974 | Dandliker et al. |
| 3,838,338 A | 9/1974 | Khoury |
| 3,875,518 A | 4/1975 | Odams |
| 3,930,199 A | 12/1975 | Valis |
| 3,942,123 A | 3/1976 | Georgi |
| 3,943,460 A | 3/1976 | Arai |
| 4,041,387 A | 8/1977 | Dalichow et al. |
| 4,051,434 A | 9/1977 | Sweet |
| 4,053,839 A | 10/1977 | Knoedl |
| 4,063,169 A | 12/1977 | Palmer |
| 4,130,799 A | 12/1978 | Cherry |
| 4,137,497 A | 1/1979 | Lowenschuss |
| 4,139,819 A | 2/1979 | Worley |
| 4,139,870 A | 2/1979 | Tachi |
| 4,144,490 A | 3/1979 | Stevens |
| 4,150,432 A | 4/1979 | Sorden |
| 4,169,213 A | 9/1979 | Dye et al. |
| 4,310,891 A | 1/1982 | Niki |
| 4,339,722 A | 7/1982 | Sydor et al. |
| 4,345,206 A | 8/1982 | Skalka |
| 4,368,354 A | 1/1983 | Furihata et al. |
| 4,374,358 A | 2/1983 | Hirose |
| 4,389,642 A | 6/1983 | Kahn |
| 4,420,809 A | 12/1983 | Pierce |
| 4,494,067 A | 1/1985 | Barszczewski |
| 4,514,592 A | 4/1985 | Miyaguchi |
| 4,544,892 A | 10/1985 | Kaufman et al. |
| 4,546,490 A | 10/1985 | Miller-Thomson et al. |
| 4,583,211 A | 4/1986 | Nishikawa et al. |
| 4,588,979 A | 5/1986 | Adams |
| 4,603,292 A | 7/1986 | Russell |
| 4,609,990 A | 9/1986 | Sember et al. |
| 4,616,173 A | 10/1986 | Cook et al. |
| 4,651,089 A | 3/1987 | Haigh |
| 4,667,689 A | 5/1987 | Kohashi |
| 4,670,712 A | 6/1987 | Lavergnat et al. |
| 4,672,556 A | 6/1987 | Shepler |
| 4,695,791 A | 9/1987 | Miller |
| 4,695,792 A | 9/1987 | Roy |
| 4,707,653 A | 11/1987 | Wagner |
| 4,716,363 A | 12/1987 | Dukes et al. |
| 4,760,536 A | 7/1988 | Curtis |
| 4,769,836 A | 9/1988 | Aihara |
| 4,795,963 A | 1/1989 | Ueno et al. |
| 4,864,588 A | 9/1989 | Simpson et al. |
| 4,864,634 A | 9/1989 | Nakagawa et al. |
| 4,866,260 A | 9/1989 | Lescourret |
| 4,880,005 A | 11/1989 | Pless et al. |
| 4,942,365 A | 7/1990 | Satterwhite |
| 4,984,254 A | 1/1991 | Thomas |
| 5,027,228 A | 6/1991 | Yokoyama |
| 5,065,095 A | 11/1991 | Suzuki |
| 5,095,279 A | 3/1992 | Quan et al. |
| 5,122,758 A | 6/1992 | Tomita |
| 5,128,607 A | 7/1992 | Clark et al. |
| 5,157,699 A | 10/1992 | Miyazaki et al. |
| 5,168,215 A | 12/1992 | Puzzo |
| 5,206,549 A | 4/1993 | Suzuki et al. |
| 5,262,714 A | 11/1993 | Friedman |
| 5,302,916 A | 4/1994 | Pritchett |
| 5,304,938 A | 4/1994 | Gregory et al. |
| 5,313,154 A | 5/1994 | Norris |
| 5,317,215 A | 5/1994 | Kranzler |
| 5,323,096 A | 6/1994 | Nakai |
| 5,365,181 A | 11/1994 | Mair |
| 5,381,085 A | 1/1995 | Fischer |
| 5,442,278 A | 8/1995 | Fan Chiang et al. |
| 5,448,606 A | 9/1995 | Snelgrove |
| 5,471,133 A | 11/1995 | Sezi |
| 5,509,040 A | 4/1996 | Shimada |
| 5,539,355 A | 7/1996 | Nakamura |
| 5,555,247 A | 9/1996 | Matsuoka et al. |
| 5,650,954 A | 7/1997 | Minuhin |
| 5,652,552 A | 7/1997 | Chung |
| 5,710,710 A | 1/1998 | Owen et al. |
| 5,764,045 A | 6/1998 | Hayashi |
| 5,941,974 A | 8/1999 | Babin |
| 6,018,560 A | 1/2000 | Kim |
| 6,078,200 A | 6/2000 | Miyano |
| 6,127,950 A | 10/2000 | Yamauchi |
| 6,140,869 A | 10/2000 | Troise |
| 6,172,579 B1 | 1/2001 | Dacus et al. |
| 6,181,829 B1 | 1/2001 | Clark et al. |
| 6,259,251 B1 | 7/2001 | Sugiura et al. |
| 6,265,869 B1 | 7/2001 | Takahashi |
| 6,282,803 B1 | 9/2001 | Dunne |
| 6,359,938 B1 * | 3/2002 | Keevill et al. ............... 375/316 |
| 6,360,090 B1 | 3/2002 | Holcombe et al. |
| 6,377,616 B1 | 4/2002 | Brankovic et al. |
| 6,411,075 B1 | 6/2002 | Battiston et al. |
| 6,463,452 B1 | 10/2002 | Schulist |
| 6,519,194 B2 | 2/2003 | Tsujino et al. |
| 6,549,479 B2 | 4/2003 | Blodgett |
| 6,566,964 B1 | 5/2003 | Hirano |
| 6,590,400 B2 | 7/2003 | Hilliard et al. |
| 6,665,367 B1 | 12/2003 | Blair |
| 6,674,277 B1 | 1/2004 | Oishi et al. |
| 6,675,326 B1 | 1/2004 | Yoshizaki |
| 6,680,607 B2 | 1/2004 | Smith |
| 6,759,838 B2 | 7/2004 | Tao et al. |
| 6,834,093 B1 | 12/2004 | Chiu |
| 6,888,902 B1 | 5/2005 | Kondo |
| 6,917,191 B2 | 7/2005 | Oishi et al. |
| 7,027,940 B2 | 4/2006 | Iannuzzi |
| 7,046,964 B1 | 5/2006 | Sullivan et al. |
| 7,068,744 B2 | 6/2006 | Watanabe |
| 7,124,153 B2 | 10/2006 | Grushin |
| 7,230,458 B2 | 6/2007 | DaDalt |
| 7,242,223 B1 | 7/2007 | Alon |
| 7,265,559 B1 | 9/2007 | Hladky et al. |
| 7,266,756 B2 | 9/2007 | Saado et al. |
| 7,271,631 B2 | 9/2007 | Watanabe |
| 7,276,978 B2 | 10/2007 | Puma et al. |
| 7,285,961 B2 | 10/2007 | Shinmoto et al. |
| 7,372,875 B2 * | 5/2008 | Hadzic et al. ............... 370/516 |
| 7,394,723 B2 | 7/2008 | Rubin |
| 7,409,031 B1 | 8/2008 | Lee et al. |
| 7,429,896 B2 | 9/2008 | Hattori |
| 7,436,265 B2 | 10/2008 | Park et al. |
| 7,463,096 B2 | 12/2008 | Chi et al. |
| 7,466,789 B2 | 12/2008 | Rieubon et al. |
| 7,504,976 B1 | 3/2009 | Pellon |
| 7,560,962 B2 | 7/2009 | Kamath |
| 7,636,747 B2 | 12/2009 | Watanabe |
| 7,642,767 B2 | 1/2010 | Willis |
| 7,653,170 B2 | 1/2010 | Mattes et al. |
| 7,692,419 B1 | 4/2010 | Peel |
| 7,696,741 B2 | 4/2010 | Gurr |

(56) References Cited

U.S. PATENT DOCUMENTS

| | | |
|---|---|---|
| 7,729,071 B2 | 6/2010 | Harada |
| 7,737,688 B2 | 6/2010 | Tomida et al. |
| 7,750,618 B1 | 7/2010 | Fang et al. |
| 7,750,685 B1 | 7/2010 | Bunch |
| 7,804,289 B2 | 9/2010 | Li |
| 7,847,597 B1 | 12/2010 | Chan et al. |
| 7,907,016 B2 | 3/2011 | Eikenbroek |
| 7,932,751 B2 | 4/2011 | Boomer |
| 8,139,685 B2 * | 3/2012 | Simic et al. .................. 375/324 |
| 8,140,283 B2 | 3/2012 | Banmouyal et al. |
| 8,242,941 B2 * | 8/2012 | Arknæs-Pedersen et al. ............................ 341/118 |
| 8,258,831 B1 | 9/2012 | Banai et al. |
| 8,461,821 B2 * | 6/2013 | Todorokihara ............. 324/76.39 |
| 8,508,213 B2 * | 8/2013 | Todorokihara ............. 324/76.39 |
| 2001/0045868 A1 | 11/2001 | Takeyabu et al. |
| 2001/0048348 A1 | 12/2001 | Unterricker |
| 2002/0024343 A1 | 2/2002 | Moore |
| 2002/0097091 A1 | 7/2002 | Takagishi |
| 2002/0167874 A1 | 11/2002 | Hayashi |
| 2002/0180415 A1 | 12/2002 | Roth |
| 2003/0038624 A1 | 2/2003 | Hilliard et al. |
| 2003/0046064 A1 | 3/2003 | Moriya et al. |
| 2003/0062959 A1 | 4/2003 | Tsuda et al. |
| 2003/0165112 A1 | 9/2003 | Noda |
| 2003/0176932 A1 | 9/2003 | Wild |
| 2003/0184346 A1 | 10/2003 | Lamb |
| 2003/0215100 A1 | 11/2003 | Kimura et al. |
| 2004/0075425 A1 | 4/2004 | Horio et al. |
| 2004/0078737 A1 | 4/2004 | Miyamoto |
| 2004/0196052 A1 | 10/2004 | Okayasu |
| 2004/0199345 A1 | 10/2004 | Ananthanarayanan et al. |
| 2005/0025270 A1 | 2/2005 | Muhammad et al. |
| 2005/0110500 A1 | 5/2005 | Hoyte et al. |
| 2005/0147197 A1 | 7/2005 | Perrott |
| 2005/0237125 A1 | 10/2005 | Hino |
| 2005/0270043 A1 | 12/2005 | Iacob et al. |
| 2006/0084386 A1 | 4/2006 | Irie et al. |
| 2006/0120537 A1 | 6/2006 | Burnett et al. |
| 2006/0171496 A1 | 8/2006 | Nakamuta et al. |
| 2006/0246865 A1 | 11/2006 | Makarov |
| 2006/0267698 A1 | 11/2006 | Erdogan et al. |
| 2006/0285756 A1 | 12/2006 | Sugita |
| 2007/0094581 A1 | 4/2007 | Kajita |
| 2007/0103333 A1 | 5/2007 | Michalski et al. |
| 2007/0132442 A1 | 6/2007 | Jones |
| 2007/0159938 A1 | 7/2007 | Sugawara et al. |
| 2007/0216556 A1 | 9/2007 | Rieubon et al. |
| 2008/0019471 A1 | 1/2008 | Waldner |
| 2008/0068096 A1 | 3/2008 | Feng et al. |
| 2008/0104072 A1 | 5/2008 | Stampleman et al. |
| 2008/0120356 A1 | 5/2008 | Watanabe |
| 2008/0122498 A1 | 5/2008 | Furukawa |
| 2008/0136400 A1 | 6/2008 | Chi et al. |
| 2008/0136471 A1 | 6/2008 | Kamath |
| 2008/0165862 A1 | 7/2008 | Takahashi |
| 2008/0189064 A1 | 8/2008 | Yamaguchi et al. |
| 2008/0191762 A1 | 8/2008 | Seethamraju et al. |
| 2008/0204088 A1 | 8/2008 | Garlapati et al. |
| 2008/0229829 A1 | 9/2008 | Kondo |
| 2008/0247500 A1 | 10/2008 | Goto et al. |
| 2008/0256157 A1 | 10/2008 | Bostaman et al. |
| 2008/0291287 A1 | 11/2008 | Dvir |
| 2008/0320065 A1 | 12/2008 | Kan |
| 2009/0058452 A1 | 3/2009 | Tanaka et al. |
| 2009/0058468 A1 | 3/2009 | Hjelm et al. |
| 2009/0144018 A1 | 6/2009 | Chang et al. |
| 2009/0153256 A1 | 6/2009 | Jo et al. |
| 2009/0156150 A1 | 6/2009 | Deleon |
| 2009/0180527 A1 | 7/2009 | Asami |
| 2009/0192958 A1 | 7/2009 | Todorokihara |
| 2009/0237070 A1 | 9/2009 | Herselman |
| 2009/0240994 A1 | 9/2009 | Lee |
| 2009/0243736 A1 | 10/2009 | Miura et al. |
| 2009/0251129 A1 | 10/2009 | Todorokihara et al. |
| 2009/0261809 A1 | 10/2009 | Li |
| 2009/0295460 A1 | 12/2009 | Gulba et al. |
| 2009/0296878 A1 | 12/2009 | Tsai |
| 2010/0052653 A1 | 3/2010 | Lebrun |
| 2010/0054390 A1 | 3/2010 | Kim et al. |
| 2010/0091752 A1 | 4/2010 | Kemmochi et al. |
| 2010/0213924 A1 | 8/2010 | Osumi et al. |
| 2010/0289479 A1 | 11/2010 | Prance et al. |
| 2010/0295535 A1 | 11/2010 | Todorokihara |
| 2010/0295536 A1 | 11/2010 | Todorokihara |
| 2010/0295537 A1 | 11/2010 | Todorokihara |
| 2010/0315061 A1 | 12/2010 | Tomita et al. |
| 2011/0050352 A1 | 3/2011 | Kondo et al. |
| 2011/0068828 A1 | 3/2011 | Anderson et al. |
| 2011/0074514 A1 | 3/2011 | Marutani |
| 2011/0082656 A1 | 4/2011 | Todorokihara |
| 2011/0084687 A1 | 4/2011 | Todorokihara |
| 2011/0150168 A1 | 6/2011 | Tseng et al. |
| 2011/0182398 A1 | 7/2011 | Iwashita et al. |
| 2011/0235772 A1 | 9/2011 | Obkircher |
| 2012/0019301 A1 | 1/2012 | Murray |
| 2012/0053903 A1 | 3/2012 | Todorokihara |
| 2012/0161815 A1 | 6/2012 | Polivka |

FOREIGN PATENT DOCUMENTS

| | | |
|---|---|---|
| JP | 53-111768 | 9/1978 |
| JP | A-56-169923 | 12/1981 |
| JP | A-61-501528 | 7/1986 |
| JP | A-61-223662 | 10/1986 |
| JP | A-62-298726 | 12/1987 |
| JP | A-64-054271 | 3/1989 |
| JP | A-64-57189 | 3/1989 |
| JP | A-01-182758 | 7/1989 |
| JP | A-01-269297 | 10/1989 |
| JP | A-02-252306 | 10/1990 |
| JP | A-04-048271 | 2/1992 |
| JP | A-04-072815 | 3/1992 |
| JP | A-04-357468 | 12/1992 |
| JP | A-05-030772 | 4/1993 |
| JP | A 5-172861 | 7/1993 |
| JP | A-05-327515 | 12/1993 |
| JP | A-06-011525 | 1/1994 |
| JP | A-06-501554 | 2/1994 |
| JP | A-06-164372 | 6/1994 |
| JP | A-06-235743 | 8/1994 |
| JP | A-06-342021 | 12/1994 |
| JP | A-07-055554 | 3/1995 |
| JP | A-07-229910 | 8/1995 |
| JP | A-07-260526 | 10/1995 |
| JP | A-09-178785 | 7/1997 |
| JP | A-09-304259 | 11/1997 |
| JP | A-10-132874 | 5/1998 |
| JP | A-10-170566 | 6/1998 |
| JP | A-09-178785 | 7/1998 |
| JP | A-11-154921 | 6/1999 |
| JP | A-11-220369 | 8/1999 |
| JP | A-11-264846 | 9/1999 |
| JP | A-2000-307384 | 11/2000 |
| JP | A-2001-094395 | 4/2001 |
| JP | A 2001-119291 | 4/2001 |
| JP | A-2001-166008 | 6/2001 |
| JP | A-2001-177378 | 6/2001 |
| JP | A-2002-057583 | 2/2002 |
| JP | A-2003-065768 | 3/2003 |
| JP | A-2003-179490 | 6/2003 |
| JP | A-2003-194860 | 7/2003 |
| JP | A-2003-249905 | 9/2003 |
| JP | A-2003-307481 | 10/2003 |
| JP | A-2003-315356 | 11/2003 |
| JP | A-2005-020554 | 1/2005 |
| JP | A-2006-029874 | 2/2006 |
| JP | A-2006-165912 | 6/2006 |
| JP | A-2007-060447 | 3/2007 |
| JP | A-2008-131500 | 6/2008 |
| JP | A-2008-147837 | 6/2008 |
| JP | A-2009-229353 | 10/2009 |
| JP | A 2009-250807 | 10/2009 |
| JP | A-2009-250808 | 10/2009 |

(56) References Cited

FOREIGN PATENT DOCUMENTS

| | | |
|---|---|---|
| JP | A-2010-085286 | 4/2010 |
| JP | A-2010-127914 | 6/2010 |
| JP | A-2010-271210 | 12/2010 |
| JP | A-2010-271211 | 12/2010 |
| WO | WO 85-04487 A | 10/1985 |
| WO | WO 92/04634 A1 | 3/1992 |

OTHER PUBLICATIONS

Katano, K., "Introduction to Proper Method for Using Measuring Instruments; How to Use Timing Devices," Transistor Technology Seminar, 14$^{th}$ Installment, Feb. 1994, p. 331-338 (with English translation).
Oct. 11, 2011 Office Action issued in U.S. Appl. No. 12/418,000.
Office Action dated May 25, 2012 issued in U.S. Appl. No. 12/782,382.
Office Action dated May 30, 3012 issued in U.S. Appl. No. 12/783,900.
Office Action dated May 23, 2012 issued in U.S. Appl. No. 12/784,136.
Office Action dated Jun. 5, 2012 issued in U.S. Appl. No. 12/418,000.
Feb. 29, 2012 Office Action issued in U.S. Appl. No. 12/782,382.
Mar. 7, 2012 Office Action issued in U.S. Appl. No. 12/418,000.
Office Action issued Dec. 14, 2011 in U.S. Appl. No. 12/782,382.
Office Action issued Dec. 29, 2011 in U.S. Appl. No. 12/783,900.
Office Action issued Dec. 29, 2011 in U.S. Appl. No. 12/835,108.
Office Action issued Jan. 6, 2012 in U.S. Appl. No. 12/784,136.
Nov. 28, 2012 Office Action issued in U.S. Appl. No. 12/418,000.
Nov. 30, 2012 Notice of Allowance issued in U.S. Appl. No. 12/782,382.
Mar. 13, 2013 Notice of Allowance issued in U.S. Appl. No. 12/782,382.
Apr. 8, 2013 Office Action issued in U.S. Appl. No. 12/835,108.
Apr. 19, 2013 Notice of Allowance issued in U.S. Appl. No. 12/889,770.
Jun. 12, 2013 Notice of Allowance issued in U.S. Appl. No. 12/783,900.
Jul. 16, 2013 Notice of Allowance issued in U.S. Appl. No. 12/889,770.
Jul. 11, 2013 Corrected Notice of Allowability issued in U.S. Appl. No. 12/782,382.
May 9, 2013 Supplemental Notice of Allowability issue in U.S. Appl. No. 12/889,770.
Sep. 10, 2013 Notice of Allowance issued in U.S. Appl. No. 12/835,108.
Feb. 6, 2013 Notice of Allowance issued in U.S. Appl. No. 12/784,136.
Jan. 14, 2013 Advisory Action issued in U.S. Appl. No. 12/783,900.
Jan. 28, 2013 Office Action issued in U.S. Appl. No. 12/783,900.
Jan. 31, 2013 Office Action issued in U.S. Appl. No. 12/889,770.
Jul. 23, 2012 Office Action issued in U.S. Appl. No. 12/835,108.
Jul. 31, 2012 Office Action issued in U.S. Appl. No. 12/418,000.
Sep. 14, 2012 Office Action issued in U.S. Appl. No. 12/784,136.
Sep. 19, 2012 Office Action dated issued in U.S. Appl. No. 12/782,382.
Sep. 27, 2012 Office Action Issued in U.S. Appl. No. 12/783,900.
Oct. 17, 2012 Office Action issued in U.S. Appl. No. 12/889,770.
U.S. Appl. No. 12/835,108 in the name of Kondo filed Jul. 13, 2010.
U.S. Appl. No. 12/889,770 in the name of Todorokihara, filed Sep. 24, 2010.
U.S. Appl. No. 12/784,136 in the name of Todorokihara, filed May 20, 2010.
U.S. Appl. No. 12/782,382 in the name of Todorokihara, filed May 18, 2010.
U.S. Appl. No. 12/418,000 in the name of Todorokihara, filed Apr. 3, 2009.
U.S. Appl. No. 13/211,726 in the name of Todorokihara, filed Aug. 17, 2011.
Sep. 25, 2013 Office Action Issued in U.S. Appl. No. 13/211,726.

\* cited by examiner

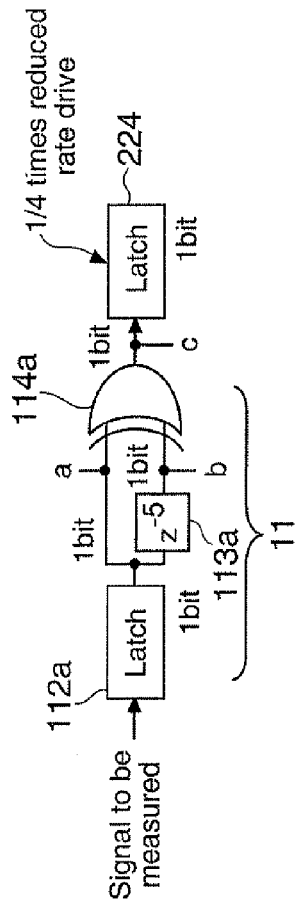

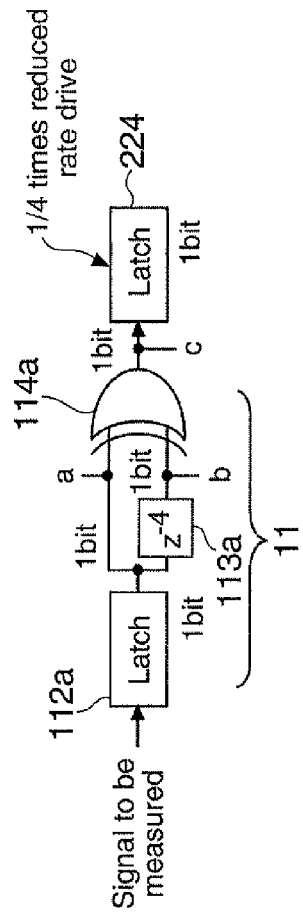

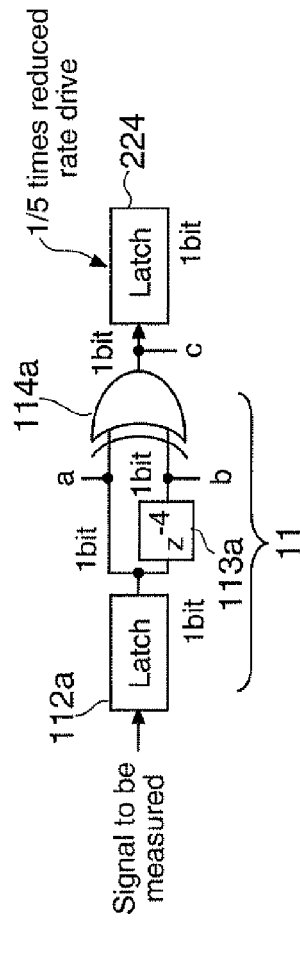

FREQUENCY MEASUREMENT METHOD, FREQUENCY MEASUREMENT DEVICE AND APPARATUS EQUIPPED WITH FREQUENCY MEASUREMENT DEVICE

The present application claims a priority based on Japanese Patent Application No. 2009-232501 filed on Oct. 6, 2009, the contents of which are incorporated herein by reference.

BACKGROUND

1. Technical Field

The present invention relates to frequency measurement devices and, more particularly, to improvements of a frequency measurement device that is capable of measuring an absolute frequency, using a frequency measurement device that counts a signal to be measured for a predetermined time, and removes high frequency components from a stream of counted values thereby detecting a frequency change component.

2. Related Art

As frequency measurement methods, a direct count method that counts pulses passing within a predetermined gate time (see, for example, JP-A-2001-119291 (Patent Document 1)), a reciprocal method that accurately measures a pulse period and obtains a frequency from its time reciprocal (see, for example, JP-A-05-172861 (Patent Document 2)), and a method that obtains a delta sigma ($\Delta\Sigma$) modulation signal to acquire a frequency (see, for example, U.S. Pat. No. 7,230,458 (Patent Document 3)) are known.

The inventors of the invention have proposed a "short-gate time count method" (see JP-A-2009-250807) as a novel frequency measurement method having characteristics that are nonexistent in the methods of related art. According to the short-gate time count method, counting (sampling) of pulses is continuously repeated with a short-gate time, and high frequency components are removed from a stream of the obtained counted values, whereby an output corresponding to the frequency of the signal to be measured is obtained. By this method, both of the time resolving power and the frequency resolving power can be considerably improved, compared to the methods of related art.

The frequency counter of the proposed method uses a short-gate counter section and a low-pass filter section that removes high frequency components. When a digital filter is used as a part of the composition of the low-pass filter, for example, the use of a moving average filter is proposed. The use of a moving average filter can substantially reduce the amount of computation, enabling highly accurate real-time measurement.

The short-gate counter section has a relatively simple hardware structure, and therefore is suitable for high-speed operation. However, the processing at the filter section needs addition and subtraction of multiple bits, such that the upper limit of sampling frequency in real time measurement is defined, mainly, by the processing power of the filter section. To obtain a moving average filter with desired characteristics, it is necessary to structure a shift register with multiple bits in multiple stages and to operate such a shift register at high speed, resulting in a greater circuit scale and greater power consumption.

SUMMARY

In accordance with an advantage of some aspects of the invention, it is possible to provide a counter (a frequency measurement device) of a short-gate time count method, wherein the structure of its low-pass filter section is simplified to achieve lower power consumption.

In accordance with another advantage of some aspects of the invention, it is possible to reduce noise generation that would likely occur, resulting from simplification of the filter structure of the low-pass filter section.

A frequency measurement device in accordance with an embodiment of the invention is equipped with a counter section that counts a supplied pulse stream signal to be measured at a predetermined time interval and outputs a stream of count values corresponding to the frequency of the signal, and a low-pass filter section that performs a filtering process on the stream of count values, wherein the low-pass filter section is formed from moving average filters in multiple stages, and an output of at least one moving average filter among the moving average filters in multiple stages is downsampled.

It is preferred that sampling frequencies for obtaining data at the moving average filters in multiple stages decrease at each of the stages of the moving average filters from the first stage to the last stage of the moving average filters.

With the composition described above, the structure of the low-pass filter section in the frequency measurement device of a short-gate time count method can be simplified. By simplifying the circuit structure of the moving average filter and lowering the operation frequency of the circuit, the number of components and the power consumption can be reduced.

The short-gate time count method used in the frequency measurement device in accordance with the present embodiment exhibits in principle a noise shaping function, and has a small change in count values when changes in the frequency of the signal to be measured are within a range sufficiently lower than the sampling frequency of the counter section, such that influence such as aliasing noise is very low, even when the data stream is intermittently processed in downsampling (decimation) by the low-pass filter section (the moving average filter).

Preferably, in the downsampling between two consecutive ones of the moving average filters in forward and rear stages, at least one of the number of data delay taps in the moving average filter in the forward stage and the sampling frequency in the moving average filter in the rear stage may be adjusted such that a cumulative value of the stream of data intermittently transmitted from the moving average filter in the forward stage to the moving average filter in the rear stage in a specified period becomes to be a constant value.

When downsampling is performed by a multiple-stage moving average filter, aliasing noise is generated. To prevent such aliasing noise, high frequency components need to be reduced to a substantially low level by inserting a low-pass filter before the downsampling. However, according to the structure of the invention, generation of aliasing noise that may occur in downsampling between the moving average filters can be avoided without providing an additional low-pass filter, such that the structure of the low-pass filter section can be simplified.

The counter section and the moving average filter in the first stage in the low-pass filter may preferably be formed from a circuit that processes a binary signal (bit-stream). This is convenient because the counter section and the moving average filter in the first stage in the low-pass filter can be simplified into a circuit with equivalent functions thereof.

The predetermined time may preferably be less than one second (more precisely, less than one second but more than an operational limit of the circuit, for example, 0.01 μsecond), without any particular limitation thereto. For example, when gate sampling of about 0.1 m second is performed, for example, the time resolving power can be expected to improve by about one to two digits and the SN ratio by about two to three digits, compared to the direct count method of related art.

A frequency measurement method in accordance with an embodiment of the invention pertains to a frequency measurement method (a short-gate time count method) including continuously measuring a signal in a pulse stream supplied at a predetermined time interval, and processing a stream of count values of the signal to be measured by a low-pass filter to obtain an output signal corresponding to the frequency of the signal to be measure, wherein the low-pass filter section is formed from moving average filters in multiple stages; sampling frequencies for acquiring data at the moving average filters in multiple stages are set to decrease at each of the stages of the moving average filters from the first stage to the last stage of the moving average filters; and, in the downsampling between two consecutive ones of the moving average filters in forward and rear stages, at least one of the number of data delay taps in the moving average filter in the forward stage and the sampling frequency in the moving average filter in the rear stage is adjusted such that a cumulative value of the stream of data intermittently transmitted from the moving average filter in the forward stage to the moving average filter in the rear stage in a specified period becomes to be a constant value.

According to the structure of the invention, frequency measurement can be conducted, while generation of aliasing noise that may occur in the frequency measurement device using the short-gate time count method can be avoided, and the device structure can be simplified by means of downsampling.

The frequency measurement device described above is small in circuit scale and is readily mountable, and is therefore suitable to be used as a resonance frequency change type sensor. For example, such sensors include acceleration sensors and pressure sensors using quartz oscillators, QCM (Quartz Crystal Microbalance) devices and the like. For example, the frequency measurement device of the invention may be applied to a QCM odor sensor with crystal oscillators whose oscillation frequencies change by adhesion of odor substance to the crystal oscillators, whereby a multiple-channel odor sensor can be readily structured.

BRIEF DESCRIPTION OF THE DRAWINGS

FIGS. 11A, 11B and 11C are figures for describing an example of signal transmission at the time of downsampling (¼ times) between the moving average filter (5 taps) in the forward stage and the moving average filter in the rear stage.

FIGS. 12A, 12B and 12C are figures for describing an example of signal transmission at the time of downsampling (¼ times) between the moving average filter (4 taps) in the forward stage and the moving average filter in the rear stage.

FIGS. 13A, 13B and 13C are figures for describing an example of signal transmission at the time of downsampling (⅕ times) between the moving average filter (5 taps) in the forward stage and the moving average filter in the rear stage.

FIGS. 14A, 14B and 14C are figures for describing an example of signal transmission at the time of downsampling (⅕ times) between the moving average filter (4 taps) in the forward stage and the moving average filter in the rear stage.

DESCRIPTION OF EXEMPLARY EMBODIMENTS

Preferred embodiments of the invention are described below with reference to the accompanying drawings. Corresponding sections in the figures are appended with the same reference numbers. It is noted that clock signal generation circuits for generating various clocks, a power supply circuit and the like are used in digital circuits described in the embodiments, but their detailed description will be omitted as they are known to those skilled in the art.

Short-Gate Time Count Method

Figure 1A:
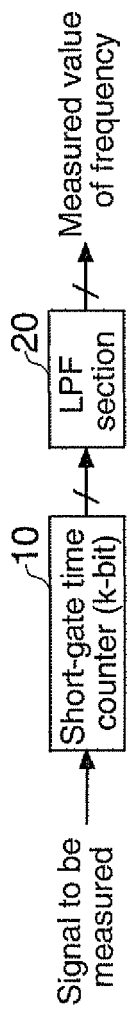
FIGS. 1A, 1B and 1C are diagrams for describing frequency measurement devices using a short-gate time count method.
Figure 1B:
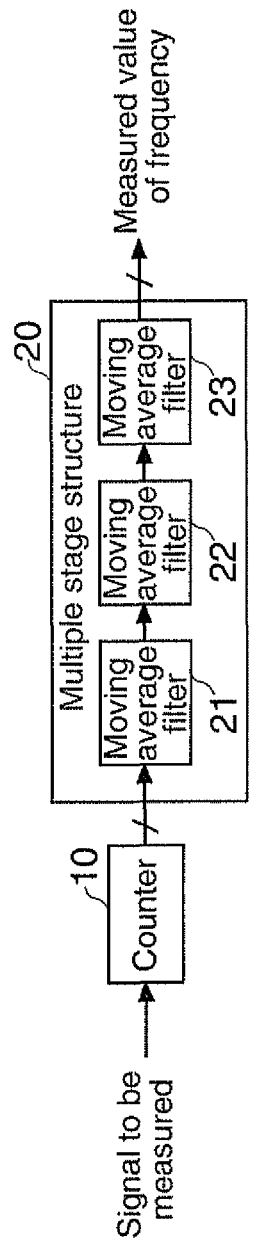
Figure 1C:
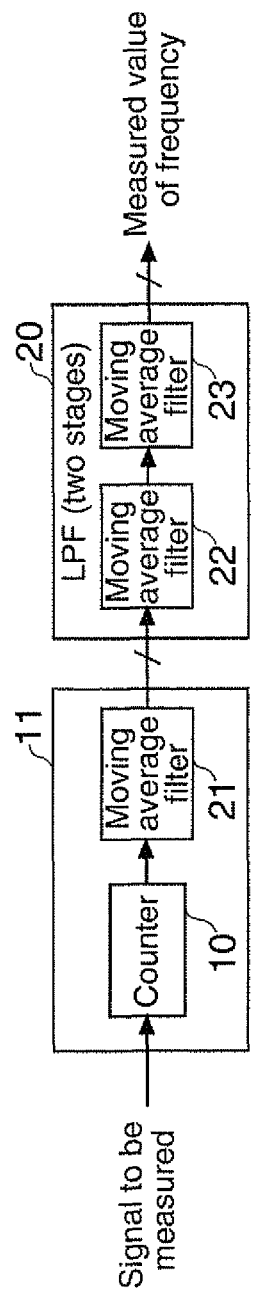

First, a short-gate time count method is described. FIGS. 1A, 1B and 1C show frequency measurement devices (frequency counters) using the short-gate time count method proposed by the inventors, for example, in Japanese Patent Application Filing No. 2008-099721 and Japanese Patent Application Filing No. 2009-123749. FIG. 1A shows a basic structure of the frequency measurement device using the short-gate time count method.

As shown in FIG. 1A, the frequency measurement device is equipped with a short-gate time counter section (hereafter also referred to as a "counter section") 10 and a low-pass filter section 20. The counter section 10 continuously counts pulses of a pulse stream signal supplied from an unshown signal source at short-gate time intervals, and continuously outputs the count values. For example, as described in Japanese Patent Application Filing No. 2008-099721, the counter operation described above may be obtained with two counters that are alternately operated at each of the gate periods whereby a count value acquired in each of the gate periods can be continuously obtained. Alternatively, an output of an up-counter equipped with a required number of digits may be latched at a gate period (a sampling period), and a counted value in the preceding measurement may be subtracted from a counted value in the current measurement, whereby a count value in each of the sampling periods can be obtained.

The low-pass filter section 20 that digitally processes the series of count values may be formed from, for example, a digital filter (or analogue filter), and may be formed from a moving average filter that performs its intended operation with a relatively small amount of computation.

Figure 2:
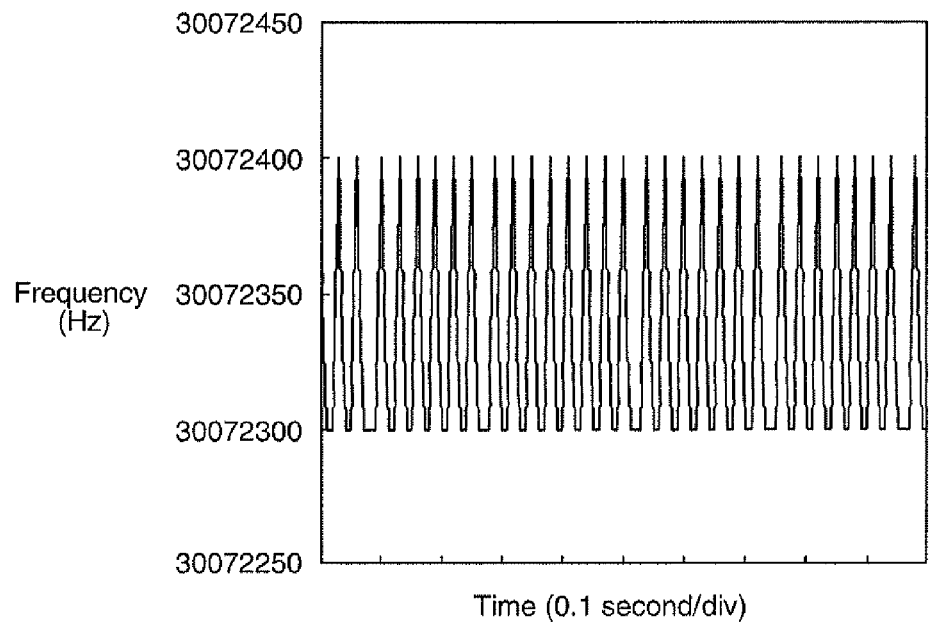
FIG. 2 is a graph for describing an example of count values given by a counter section 10.
Figure 3:
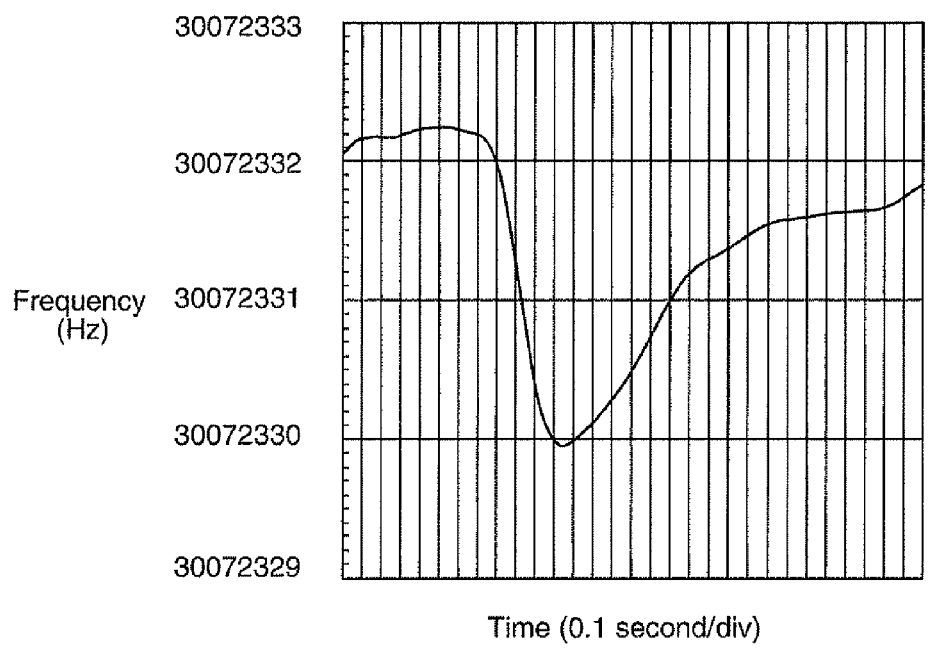
FIG. 3 is a graph showing an example of outputs of a low-pass filter section 20.

For example, FIGS. 2 and 3 show a measurement example obtained when the signal source for supplying the signal to be measured is a quartz oscillator that generates a pulse stream with an oscillation frequency of 30 MHz, the counter section 10 counts pulses with a sampling frequency of 100 Hz (a gate time of 0.01 seconds), and the low-pass filter section 20 is composed of a (digital) low-pass filter with the tap number being 512.

As shown in FIG. 2, the counter section 10 outputs a series of count values in a pulse stream. When a pulse stream signal that is stable at one spot frequency is counted, the counted values are distributed in a pulse stream having an amplitude between two values that are determined by the gate time. On the other hand, even when the frequency of a pulse stream signal to be counted changes, if the changes are within the range of quantization errors, the counted values are likewise distributed in a pulse stream with an amplitude between two values. For example, in the case of the gate time being 0.01 second, if changes in the frequency of a pulse stream signal to be counted are contained between 100 Hz and 200 Hz, a display of 100 Hz or 200 Hz can be obtained.

As shown in FIG. 3, the low-pass filter section 20 outputs low-band components which are obtained by removing pulse frequency components (high frequency components). The level of the low-band components corresponds to the frequency of the pulse stream signal (the stream of count values) supplied, and the change in the level of the low-band components corresponds to the change in the frequency of the signal to be measured. The outputs of the low-band are outputted as continuous (analog) data (curve), and frequency changes in a region that cannot be measured by counting with a sampling period at 100 Hz, in particular, frequency changes less than 1 Hz, can be detected.

In this manner, according to the short-gate time count method, a signal to be measured is continuously sampled with a short-gate time (for example, less than one second), whereby the stream of count values obtained behaves as a pulse stream signal, and the frequency (density) of the pulse stream varies according to changes in the frequency of the signal to be measured. Also, the magnitude of the oscillation frequency of the signal to be measured corresponds to the magnitude of the pulse stream. Information about the frequency of a pulse stream signal to be counted exists in low-band components of the frequency spectrum of the stream of count values that behaves as a pulse stream. Accordingly, the low-band components are extracted (harmonic components originating from quantization errors are removed) from the count values by a low-pass filter, whereby the information about the frequency of the pulse stream signal counted can be decoded.

In the frequency measurement device using the method of the present embodiment, when the low-pass filter 20 for removing high frequency components is structured with digital filters, filters in a high order (a high tap number) may preferably be used in order to acquire smooth outputs. Also, the low-pass filter section 20 may be structured in multiple stages.

The short-gate count section 10 can be realized with a relatively simple hardware structure, and therefore is suitable for high-speed operation. However, the data processing at the filter section 20 needs addition and subtraction of multiple bits. Therefore the upper limit of sampling frequency in real time measurement is defined, mainly, by the processing power of the filter section. Also, when digital filters in two or more stages are used, multiple-bit shift registers in multiple stages need to be operated at high speed, resulting in greater power consumption.

First Embodiment Example

The first embodiment example of the invention attempts to achieve higher operation speed and lower power consumption by simplifying the circuit structure of the low-pass filter section 20 in the frequency measurement device of the short-gate time count method and by gradually reducing the operation frequency of the multiple-stage filters (at least in one stage).

FIG. 1B shows an example of the structure in which the low-pass filter section 20 of the frequency measurement device shown in FIG. 1A is structured with moving average filters 21-23 in multiple stages (three stages in this embodiment).

FIG. 1C shows an example of the structure in which the counter section 10 and the moving average filter 21 of the frequency measurement device shown in FIG. 1B are combined to form a count filter section 11, and the low-pass filter section 20 is structured with moving average filters 22 and 23. By combining the counter section 10 and the moving average filter 21, the functions of a counter and a filter can be realized with a simplified circuit structure. Any schemes for simplifying digital circuits known to those skilled in the art can be used. For example, FIGS. 3-8 of Japanese Patent Application Filing No. 2009-123749 show an example of circuit simplification.

Figure 4:
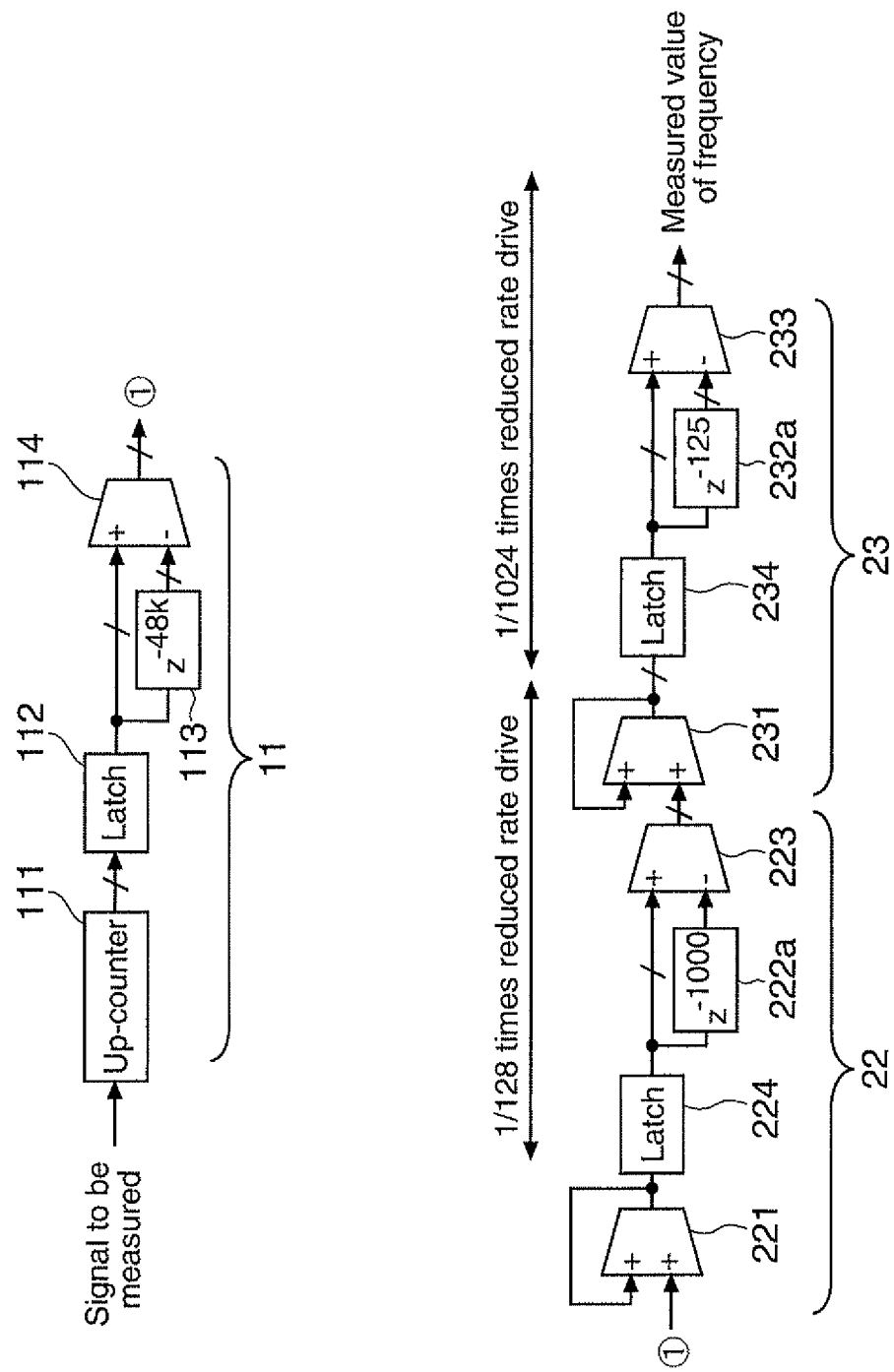
FIG. 4 is a diagram for describing an example structure in which the frequency measurement device of a short-gate time count method is formed from a count filter section and a downsampling multiple-stage moving average filter.

FIG. 4 shows an example structure of the frequency measurement device in which the simplified count filter section 11 and a multiple-stage moving average filter (moving average filters in a three-stage structure (11, 22 and 23 as a whole device structure)) are operated at lower speeds from the first stage to the rear stage, and the number of taps is also gradually reduced from the first stage to the rear stage. In this example, the short-gate time counting is conducted at 152 kHz (fs), and the cut-off frequency of the (three-stage) low-pass filter is designed to be about 0.25 Hz (without any particular limitation thereto).

In FIG. 4, the count filter section 11 is formed from an up-counter 111 that counts pulses of the signal to be measured, a data latch 112 that acquires count values of the up-counter 111 in synchronism with a sampling clock with a frequency of 152 kHz (=fs), a 48 k-stage register 113 that delays the output of the data latch 112 in synchronism with the sampling clock, and a subtractor 114 that subtracts the output of the shift register 113 from the output of the data latch 112. The count filter section 11 functions as the short-gate counter 10 that counts the pulse stream of the signal to be measure and a 48 k-tap moving average filter 21 in the first stage operated at 152 kHz (see FIG. 1C).

The output of the count filter section 11 (the output of the subtractor 114) is supplied to the second stage moving average filter 22 with the tap number being 1000 operating at a sampling frequency of 1188 Hz (=fs/128), and the output of the second-stage moving average filter 22 is supplied to the third-stage moving average filter 23 with the tap number being 125 operating at a sampling frequency of 148 Hz (=fs/1024). The output of the third-stage moving average filter 23 is the measured value of the frequency.

The moving average filter 22 is formed from an accumulator (an integrator) 221 that sequentially adds (accumulates) outputs of the subtractor 114, a data latch 224 that acquires the output of the accumulator 221 in synchronism with a sampling clock at a sampling frequency of 1188 Hz (=fs/128), a 1000-stage shift register 222a that delays the output of the data latch 224 in synchronism with the sampling clock, and a subtractor 223 that subtracts the output of the shift register 222a which is a 1000-data-preceding cumulative value from the cumulative value outputted from the data latch 224 thereby outputting a value corresponding to the moving average. Like the moving average filter 22, the moving average filter 23 is also formed from an accumulator (an integrator) 231 that accumulates outputs of the subtractor 223 in the preceding stage, a data latch 234 that acquires the output of the accumulator 231 in synchronism with a sampling clock at a sampling frequency of 148 Hz (=fs/1024), a 125-stage shift register 232a that delays the output of the data latch 234 in synchronism with the sampling clock, and a subtractor 233 that subtracts the output of the shift register 232a which is a 125-data-preceding cumulative value from the cumulative value outputted from the data latch 234 thereby outputting a value corresponding to the moving average.

It is noted that, in accordance with the present embodiment, the low-pass filter section 20 is structured with moving average filters in three stages, and downsampling is conducted in two stages. However, the invention is not limited to such a structure. The moving average filter may be structured in a greater number of stages, and the downsampling may be conducted in greater frequency. Also, (at least) one downsampling operation is effective in reducing the number of taps. The same characteristics are similarly applicable to embodiment examples to be described below.

Comparison Example with Respect to First Embodiment Example

Figure 5:
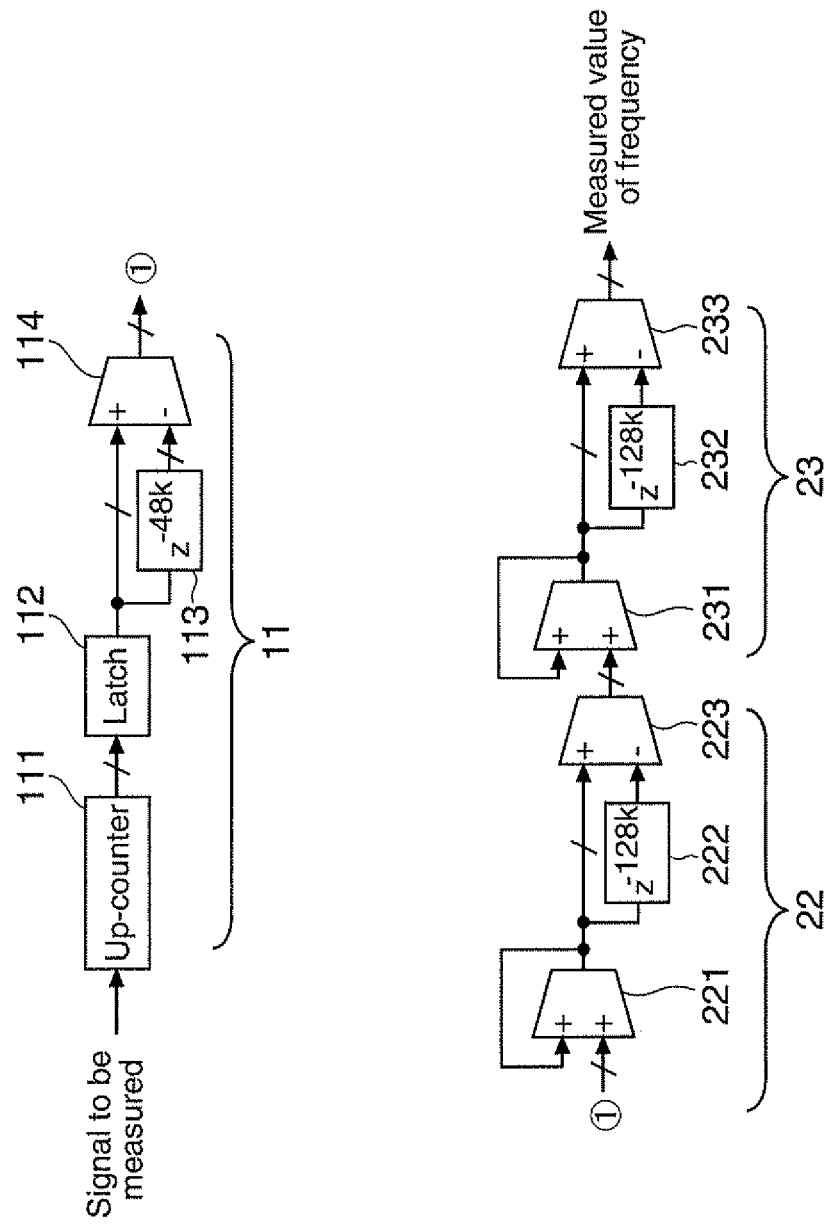
FIG. 5 is a diagram for describing an example structure for comparison in which the frequency measurement device shown in FIG. 4 is formed from a non-downsampling multiple-stage moving average filter.

FIG. 5 shows, as a comparison example, a frequency measurement device in which the frequency measurement device shown in FIG. 4 is formed from an ordinary moving average filter (in non-gradual rate reducing operation). Portions corresponding to those shown in FIG. 4 are appended with the same reference numerals. The frequency measurement device of this example is also designed such that the short-gate time count is performed at 152 kHz (fs), and the cut-off frequency of the (three-stage) low-pass filter is set to be about 0.25 Hz.

According to the structure of the comparison example, the number of taps of the three-stage low-pass filter is 152 kHz÷0.25÷2=304 k taps, wherein 48 k taps are assigned to the first-stage register 113, 128 k taps to the second-stage register 222a, and 128 k taps to the third-stage register 232, and each of the stages is operated with a sampling frequency of 152 kHz (fs). According to the embodiment of the invention, the frequency measurement device (FIG. 4) combines the short-gate time counter and the moving average filters in multiple stages in which their operation frequencies are gradually reduced, whereby the number of registers to be used is considerably reduced and the operation frequency is gradually lowered, and it is therefore understood that the power consumption is reduced.

In general, when downsampling is performed by a multiple-stage moving average filter, aliasing noise is generated. To prevent such aliasing noise, high frequency components need to be reduced to a substantially low level by inserting a low-pass filter before the downsampling. For example, an example of such technology is described in Japanese Laid-open Patent Application 2000-307384. According to the short-gate time count method, the noise shaping function can be exhibited even when downsampling is conducted. Accordingly, the low-pass filter required before the downsampling does not need high performance, compared to the case where the noise shaping function does not work. Therefore, the structure of the low-pass filter can be simplified. Also, it is acceptable if the low-pass filter section including low-pass filters before and after downsampling as a whole has a sufficient performance.

Second Embodiment Example

Figure 6:
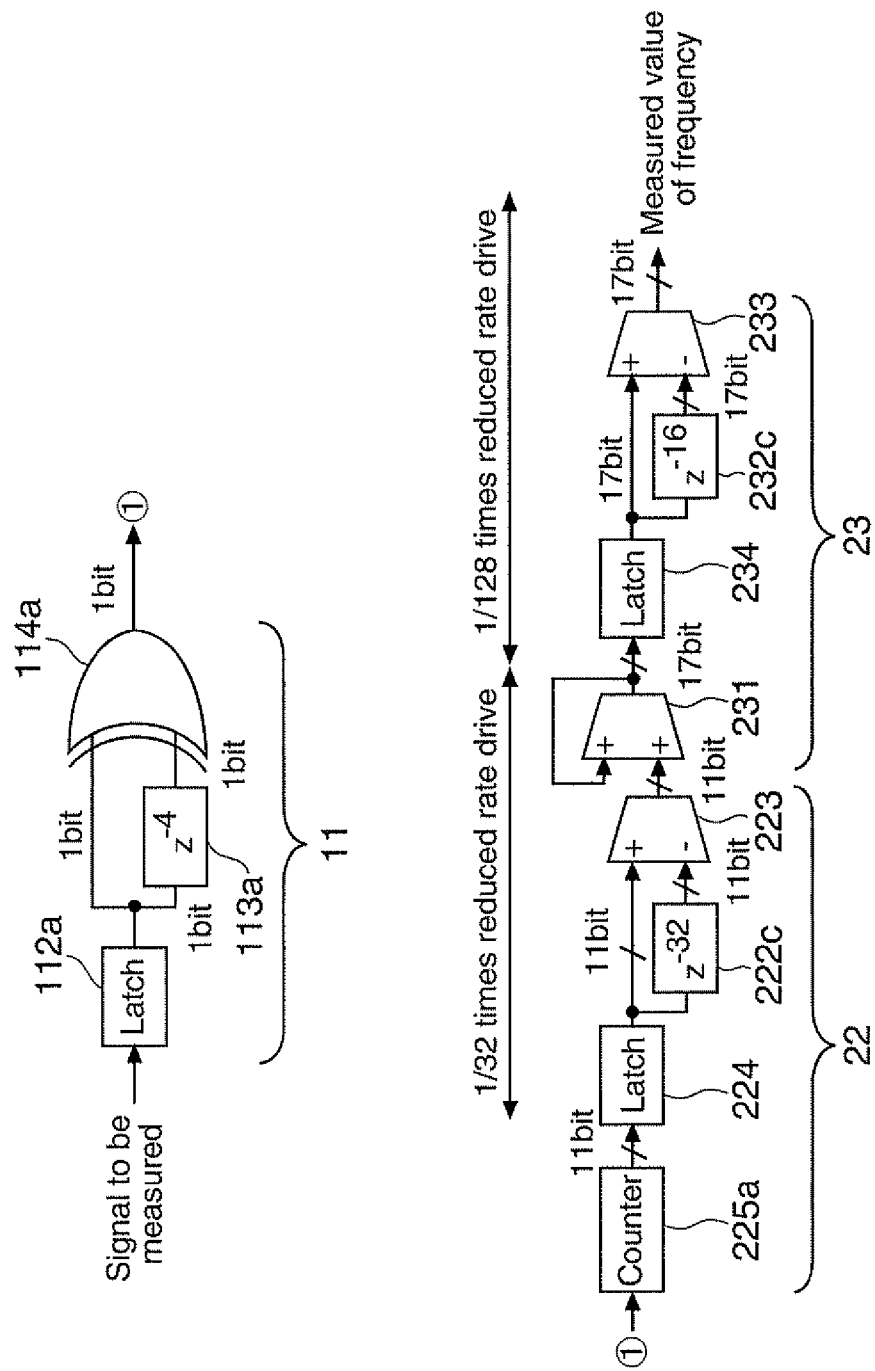
FIG. 6 is a diagram for describing an example structure in which the frequency measurement device using a short-gate time count method is formed from a bit-stream count filter section and a downsampling multiple-stage moving average filter.

FIG. 6 shows a second embodiment example of the invention, which is different from the first embodiment in that the count filter section 11 is formed from a 1-bit (binary) signal processing circuit, thereby simplifying the circuit. In this example, the short-gate time counting is conducted at 4760 Hz (fs), and the cut-off frequency of the (three-stage) low-pass filter is designed to be about 0.77 Hz. Therefore, the count filter section 11 operates at a sampling frequency of 4760 Hz (=fs), the second-stage moving average filter 22 is formed from a moving average filter with the tap number being 32 operating at a sampling frequency of 149 Hz (=fs/32), and the third-stage moving average filter 23 is formed from a moving average filter 23 with the tap number being 16 operating at a sampling frequency of 37 Hz (=fs/128). Components in FIG. 6 that correspond to those shown in FIG. 4 are appended with the same reference numerals.

According to the present example, the count filter section 11 is formed from a data latch 112a that acquires instantaneous values of a pulse stream signal to be measured (78 MHz) in synchronism with a sampling clock of 4760 Hz (fs), a 1-bit 4-stage delay shift register 113a that delays the output of the data latch 112a in synchronism with the sampling clock (fs), and an exclusive OR (EXOR) circuit 114a that adds the output of the data latch 112a and the output of the shift register 113a. The count filter section 11 functions as a 1-bit short-gate counter 10 that counts the pulse stream of the signal to be measured and the 1-bit 4-stage moving average filter in the first stage (see FIG. 1C). The output of the count filter section 11 (the output of the adder 114a) is supplied to the second-stage moving average filter 22.

The second-stage moving average filter 22 is formed from a 1-bit input and 11-bit output counter 225a that continuously performs counting, a data latch 224 that acquires the 11-bit data, a 32-stage delay shift register 222c that delays the 11-bit data, and an 11-bit output subtractor 223 that receives the output of the latch 224 as a positive input and the output of the register 222c as a negative input. The second-stage moving average filter 22 operates as a low-pass filter in synchronism with a sampling clock of (1/32) fs. The output of the second-stage moving average filter 22 (the output of the subtractor 223) is supplied to the third-stage moving average filter 23.

The moving average filter 23 is formed from a 17-bit output accumulator (an integrator) 231 that accumulates outputs of the subtractor 223 in the preceding stage, a 17-bit output data latch 234 that acquires the output of the accumulator 231 in synchronism with a sampling clock at a sampling frequency of 37 Hz (=fs/128), a 16-stage shift register 232c that delays the output of the data latch 234 in synchronism with the sampling clock, and a subtractor 233 that subtracts the output of the shift register 232c which is a 16-data-preceding cumulative value from the cumulative value outputted from the data latch 234 thereby outputting a value corresponding to the moving average.

Comparison Example with Respect to Second Embodiment Example

Figure 7:
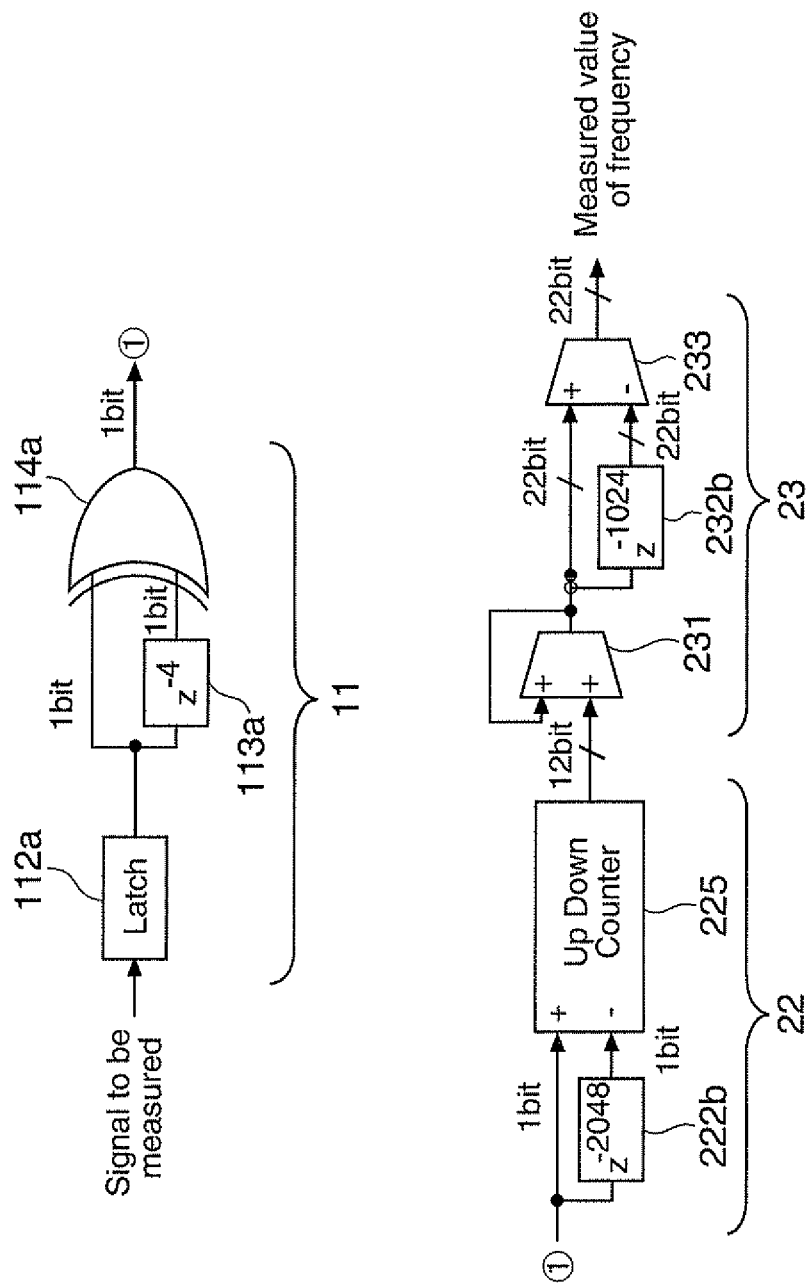
FIG. 7 is a diagram for describing an example structure for comparison in which the frequency measurement count device shown in FIG. 6 is formed from a non-downsampling multiple-stage moving average filter.

FIG. 7 shows, as a comparison example, a frequency measurement device in which the frequency measurement device shown in FIG. 6 is formed from an ordinary moving average filter (in non-gradual rate reducing operation). Portions corresponding to those shown in FIG. 6 are appended with the same reference numerals. The frequency measurement device of this example is also designed such that the short-gate time count is performed at 4760 kHz (fs), and the cut-off frequency of the (three-stage) low-pass filter is set to be about 0.77 Hz, like the second embodiment example.

According to this comparison example, the count filter section 11 is composed of a binary signal (bit stream) processing circuit, like the circuit shown in FIG. 6. The second-stage moving average filter 22 is formed from a 2048-stage shift register 222b that delays the 1-bit output of the count filter section 11 in synchronism with a sampling clock (fs), and a 12-bit output up-down counter 225 that receives the output of the count filter section 11 as an up-input and the output of the shift register 222b as a down-input. The third-stage moving average filter 23 is formed from a 22-bit output accumulator (an integrator) 231 that accumulates outputs of the filter in the preceding stage, a 1024-stage shift register 232b that delays the output of the accumulator 231 in synchronism with a sampling clock (fs), and a 22-bit output subtractor 233 that subtracts the output of the shift register 232b which is a 1024-data-preceding cumulative value from the cumulative value outputted from the accumulator 231 thereby outputting a value corresponding to the moving average.

According to the structure of the comparison example, to set the cut-off frequency of the three-stage low-pass filter at about 0.77 Hz (=4760 Hz÷(4+2048+1024)÷2), 4 taps are assigned to the first-stage register 113, 2048 taps to the second-stage register 222a, and 1024 taps to the third-stage register 232, and each of the stages is operated with a sampling frequency of 4760 Hz (fs).

According to the structure of the present embodiment, 4 taps are assigned to the first-stage register 113, 32 taps to the second-stage register 222a, and 16 taps to the third-stage register 232, and the stages are operated with sampling frequencies of 4760 Hz, 149 Hz (=fs/32) and 37 Hz (=fs/128), respectively.

Therefore, according to the embodiment of the invention, the frequency measurement device (FIG. 6) combines the short-gate time counter and the moving average filters in multiple stages in which their operation frequencies are gradually reduced, such that the number of registers to be used is considerably reduced and the operation frequency is gradually lowered, whereby the power consumption is reduced.

Comparison of Effects

Figure 8:
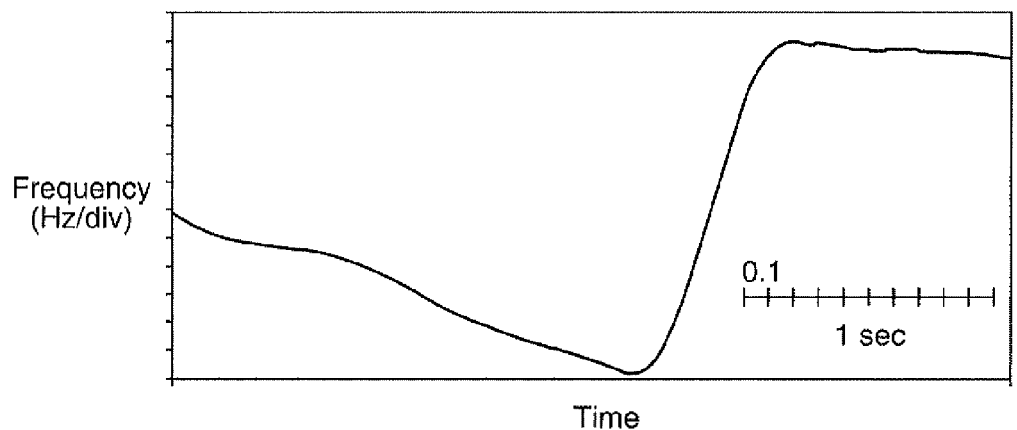
FIG. 8 is a graph for describing an example of frequency measurement given by a frequency measurement device in accordance with a second embodiment example (FIG. 6).
Figure 9:
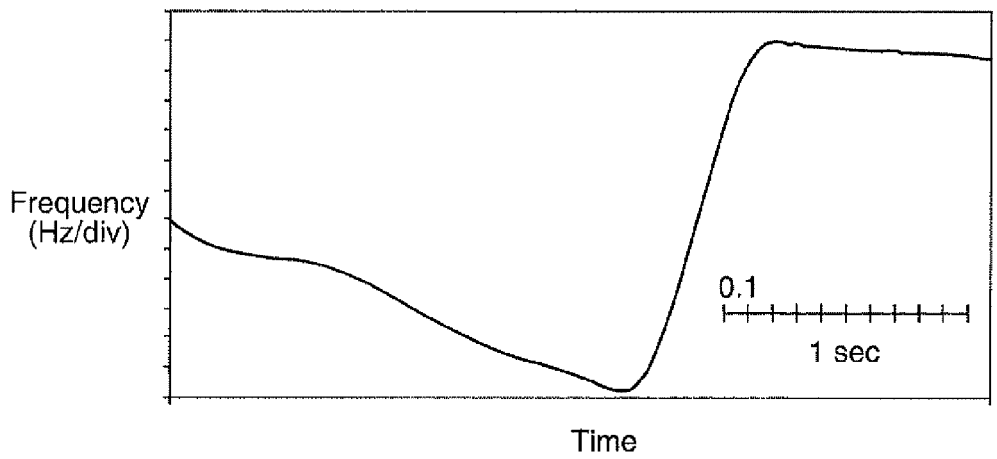
FIG. 9 is a graph for describing an example of frequency measurement given by a frequency measurement device in accordance with a comparison example (FIG. 7).

FIG. 8 is a graph showing a measurement example obtained with a frequency measurement device in accordance with the second embodiment example shown in FIG. 6 (a bit-stream counter filter+gradual downsampling of moving average filters) formed on a FPGA (Field Programmable Gate Array), wherein the short-gate counter is operated at 4760 Hz, and changes in the frequency (a signal to be measured) of a 78 MHz crystal oscillator are measured. FIG. 9 is a graph showing a measurement example obtained with a frequency measurement device of the comparison example shown in FIG. 7 (a bit-stream counter filter+non-downsampling of moving average filters) formed on a FPGA, wherein changes in the frequency (a signal to be measured) of a 78 MHz crystal oscillator are measured.

Comparing FIG. 8 with FIG. 9, it is understood that the measurement by the method of the embodiment example (short-gate time count method+downsampling) sufficiently follows the changes in the frequency of the signal to be measured, like the measurement by the method of the comparison example (short-gate time count method+non-downsampling).

The downsampling described above can be performed multiple times between adjacent stages of the multiple-stage moving average filters. Also, the downsampling may be performed once between any one of the adjacent stages thereof.

Third Embodiment Example

Next, referring to FIGS. 10 through 14, examples of methods for improving the S/N ratio of the frequency measurement device by appropriately adjusting (tuning) the tap number of the multiple-stage moving average filter and downsampling frequency of the frequency measurement device that combines the short-gate time count method and downsampling.

In accordance with the third embodiment example, in the frequency measurement device using the short-gate time count method described in the first and second embodiment examples (having a low-pass filter composed of moving average filters in multiple stages wherein sampling frequencies for acquiring data at the moving average filters at the respective stages are set to gradually lower from the first stage toward the last stage), in downsampling between two forward and rear moving average filters, the number of data delay stages in the moving average filter in the forward stage or the sampling frequency in the moving average filter in the rear stage is adjusted, such that a cumulative value of the stream of data intermittently transmitted from the moving average filter in the forward stage to the moving average filter in the rear stage in a specified period becomes to be a constant value.

Figure 10:
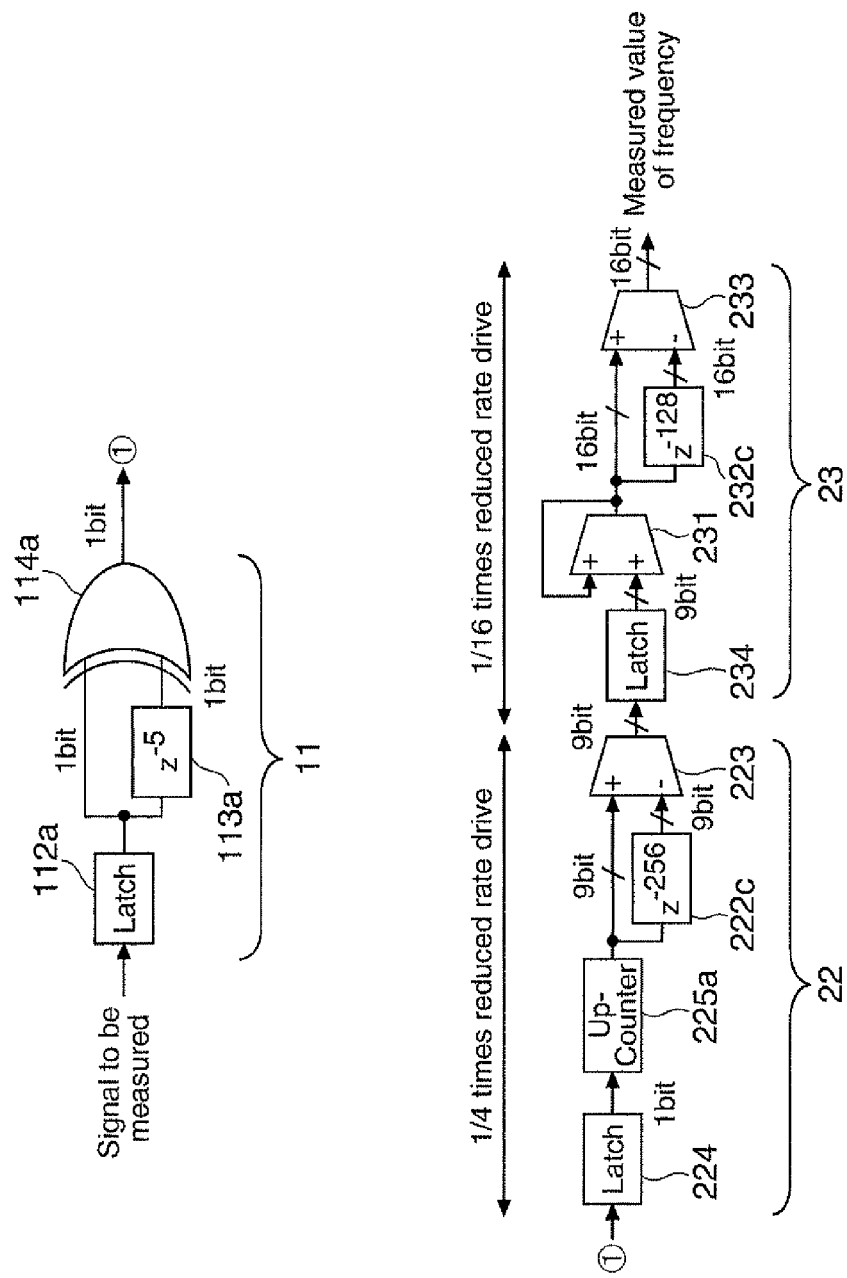
FIG. 10 is a diagram for describing a tuning method for the count filter section and the downsampling multiple-stage moving average filter of the frequency measurement device.

FIG. 10 is a diagram for describing the frequency measurement device in accordance with the third embodiment example. Components in FIG. 10 that correspond to those shown in FIG. 6 are appended with the same reference numbers, and their description shall be omitted.

In FIG. 10, the register (of the first-stage moving average filter) of the counter filter section 11 is structured with 5 taps (5 stages), for the convenience of description. Also, for the convenience of description, the data latch 224 is arranged before the up-counter 225a of the second-stage moving average filter 22, and the data latch 234 is arranged before the accumulator 231 of the third-stage moving average filter 23, which are different from the example shown in FIG. 6. The first-stage moving average filter 11 operates with a sampling frequency fs, the second-stage moving average filter 22 operates with a sampling frequency of ($\frac{1}{4}$) fs, and the third-stage moving average filter 23 operates with a sampling frequency of ($\frac{1}{16}$) fs. The number of bits on each of the signal lines is appropriately set. Other parts of the composition are substantially the same as those of the second embodiment example, and their description is therefore omitted.

FIGS. 11A, 11B and 11C are figures for describing an example of signal transmission in downsampling at the connection section between the first-stage moving average filter 11 and the second-stage moving average filter 22. FIG. 11A shows a section around the first-stage moving average filter 11 that operates with a sampling frequency fs and the data latch 224 in the rear stage that operates with a sampling frequency of ($\frac{1}{4}$) fs. Also, the output of the data latch 112a is shown as a portion a (to be described below), and the output of the shift register 113a is shown as a portion b (to be described below). Also, the output of the adder (EXOR) in which these inputs are inputted (the input to the data latch 224) is shown as a portion c FIG. 11B shows signal transmission examples at the respective portions shown in FIG. 11A. When the data latch 112a of the short-gate counter section successively acquires instantaneous values of the signal to be measured in synchronism with clocks 1-34 of the sampling frequency fs, and outputs corresponding data (0 or 1), the portion a, the portion b, the portion c and the latch 224 in the rear stage operating at (fs/4) have data as shown in the tables. The latch 224 intermittently acquires data from the series of data stream outputted from the adder 114a according to the sampling frequency (fs/4). Outputs of the latch 224 at clocks 0-34 (in a specified period) are added by the up-counter in the rear stage (corresponding to an accumulator) 225a. As described below, the interval (downsampling) for acquiring data is adjusted according to the SN ratio of the output of the moving average filter.

FIG. 11C shows a case where the signal to be measured is affected by jitter (time axis jitter in the signal) and the like, and the input values of bits at the clocks 18 and 19 are switched with each other. When no jitter occurs (FIG. 11B), the value of the counter 225a, which is an accumulation of outputs of the data latch 224 of the second-stage moving average filter 22, is "4." However, when jitter occurs and the output values "1" and "0" at the clock 18 and 19 are switched with each other, the cumulative value of the data latch 224 in the rear stage (the value of the counter 225a) becomes to be "5" (see FIG. 11C). This corresponds to an incident in which noise is generated by the influence of jitter. The input of "1" at the clock 18 or the input of "1" at the clock 19 has a different impact (contribution) to the cumulative value in the rear stage.

FIG. 12 shows a case where the number of taps (stages) of the shift register 113a of the first-stage moving average filter is changed to "4." Other parts of the composition are the same as those shown in FIG. 11.

In this case, the latched value of the second-stage moving average filter 22 at the clock 18 changes to "0," but the latched value of the second-stage moving average filter section at the clock 22 changes to "1," such that the number of cells having the value "1" of the output of the data latch 224 in a specified period does not change. In other words, the input of "1" at the clock 18 (FIG. 12C) or the input of "1" at the clock 19 (FIG. 12B) causes the same result. This is equivalent to having the noise shaping function.

Accordingly, by adjusting the number of taps of the shift register 113a, noise shaping can be functioned. In other words, when the data latch 112a is influenced by jitter, a time shift (a phase difference) occurs in the output value of the adder 114a. However, as long as the consistency between the phase difference and the timing of the data latch 224 is maintained, no difference occurs in the cumulative value, and therefore noise shaping works. For example, the number of taps of the shift register 113a can be selected to be a multiple of the downsampling.

Figures 13A, 13B, 13C:
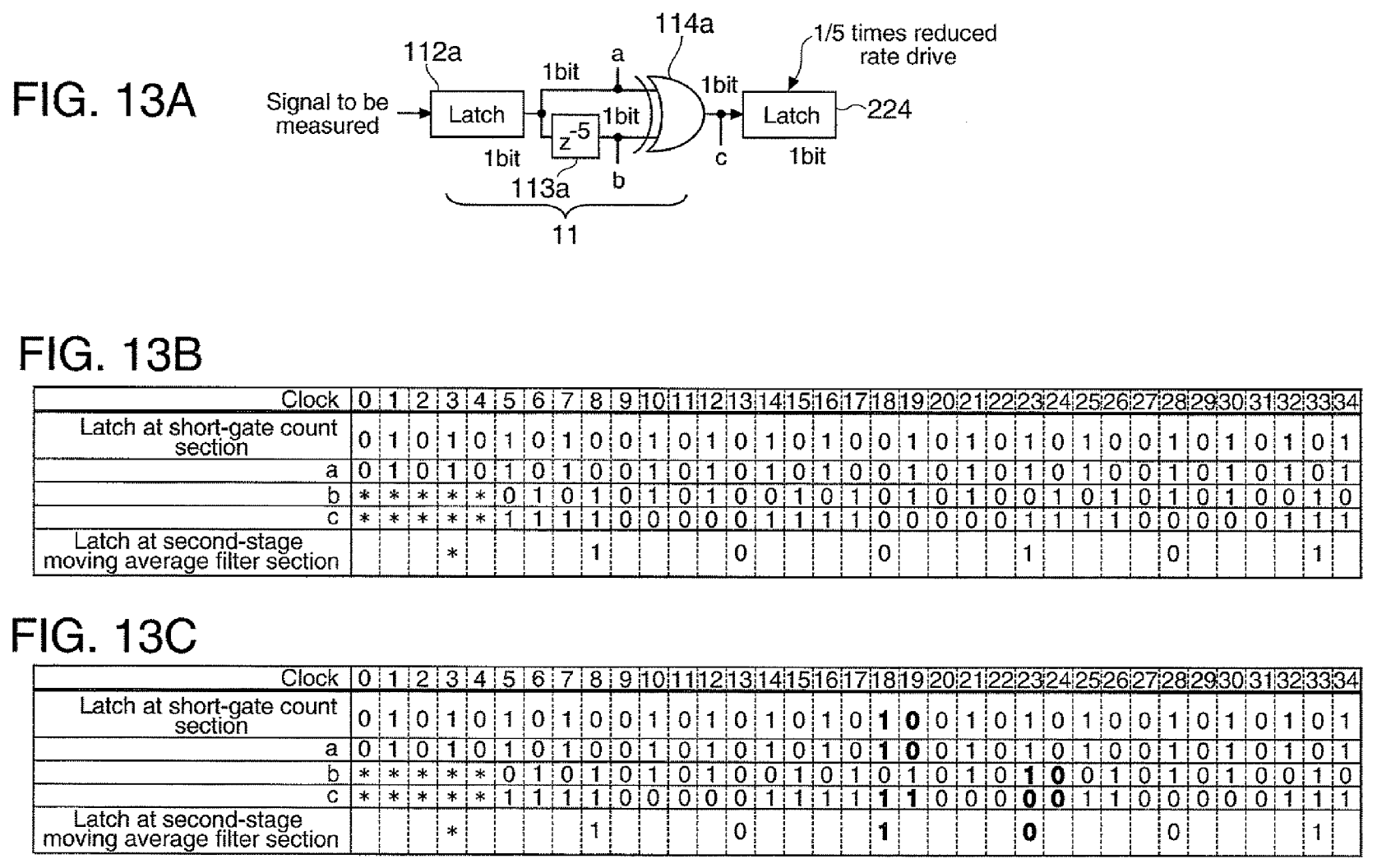

FIG. 13 shows an example in which the sampling frequency of the second-stage moving average filter 22 in the structure of FIG. 11 is set to fs (⅕). In this case, the cumulative value of the data latch 224 of the second-stage moving average filter 22 (the value of the counter 225a) is "3" without regard to the presence or absence of jitter at the clocks 18 and 19. The input of "1" at the clock 18 (FIG. 13C) or the input of "1" at the clock 19 (FIG. 13B) results in the same cumulative value (see FIGS. 13A and 13B).

FIG. 14 shows an example in which, in the structure of FIG. 11, the number of taps (stages) of the shift register 113a is set to 4 stages, and the sampling frequency of the data latch 224 in the rear stage is set to fs (⅕). The figure shows that the signal to be measured is affected by jitter (time axis jitter of the signal) or the like, and bits of the input values are switched at the clocks 18 and 19. When no jitter occurs (FIG. 14B), the value of the counter 225a which is a cumulative value of outputs of the data latch 224 of the second-stage moving average filter 22 in a specified period is "2." However, when jitter occurs and the output values "1" and "0" of the data latch 112a at the clocks 18 and 19 are switched with each other, the cumulative value of the data latch 224 in the rear stage becomes "3" (FIG. 14C). This corresponds to an incident in which noise is generated by influence of the jitter. The input of "1" at the clock 18 or the input of "1" at the clock 19 has a different impact (contribution) to the cumulative value in the rear stage.

Accordingly, S/N can be improved by adjusting the interval of downsampling (sampling frequency), the phase difference between the time axis of the series of data stream and the time axis of downsampling timing (a shift in the sampling position) and the like. For example, the number of taps of the shift register 113a may be selected to be a multiple of downsampling, and the downsampling period may be selected to be one of divisors of the number of taps of the shift register 113a.

It goes without saying that both of the data shift amount (the filter's tap number) and the sampling frequency (period) of downsampling may be adjusted.

In the case of FIG. 11, as the ±1 count error at the time of measurement is not corrected and therefore the noise shaping effect cannot be obtained, it is understood that the ±1 count error is transferred as is. The ±1 count error generated in this instance corresponds to an input error of ±4760 Hz (which is the same value as the sampling frequency). As this error is transferred as is to the blocks in succeeding stages, the ±1 count error is outputted in a form having being smoothed by the moving average filter.

An absolute value of the impact of the ±1 count error on the output can be roughly estimated as a maximum value of the impulse response from the tap number of the moving average filter and the operation clock, which is 4760 Hz÷(128×16)≅ 2.3 Hz. On the other hand, an absolute value (a theoretical value) of the error is $(1/\sqrt{(4760)})\div((5+256\times4+128\times16)\div4760)\cong 0.02$ Hz. Therefore, it is understood that, according to the third embodiment example, the SN ratio of the output signal can be considerably improved.

In the third embodiment example described above, the count filter section 11 is formed with a 1-bit signal processing (bit stream) circuit structure, for the convenience of description, but the invention is not limited to such a structure. The count filter section 11 may be structured with a multiple-bit signal processing system, like the structure shown in FIG. 4.

In the above-described embodiment example (for tuning) is described with reference to an example in which downsampling is performed between the first-stage moving average filter and the second-stage moving average filter. However, the same method is similarly applicable to downsampling between the second-stage moving average filter and the third-stage moving average filter. Also, the same method is similarly applicable to downsampling between any adjacent ones of the moving average filters in multiple stages.

Accordingly, as described in the third embodiment example, by adjusting at least one of the data shift and the sampling frequency (period), the cumulative value in a specified period in the data stream becomes to be a constant value, whereby generation of noise due to quantization errors can be suppressed. For example, in the case of a sensor using quartz oscillators, characteristics of a generated signal to be measured, such as, the frequency of the signal to be measured, the range of changes in the frequency and the like, are known in advance, at least one of the number of data delay stages in a moving average filter in a forward stage and the sampling frequency of a moving average filter in a rear stage in moving average filters in multiple stages may be adjusted, whereby the S/N of the frequency measurement device can be improved.

Applied Apparatuses

The frequency measurement device in accordance with any one of the embodiments of the invention is applicable to a variety of resonance frequency change type sensors, whereby size-reduction, weight-reduction, higher resolving power and lower cost of the apparatuses can be achieved. Also, the invention is suitable for circuit integration and platform implementation of various sensors. Moreover, the invention is favorably used for transducer arrays of odor sensors, gas sensors, biosensors and the like, QCM devices, pressure sensors, acceleration sensors and the like.

Effect of Embodiment Example

As described above, in accordance with the first embodiment example of the invention, the low-pass filter using the short-gate time count method is structured with moving average filters in multiple stages, and downsampling is performed between the forward stage and the rear stage, or between any adjacent ones of the stages, such that the number of shift registers can be reduced, compared to the structure of related art composed of a short-gate counter and moving average filters.

In accordance with the second embodiment example, the short-gate time counter and the first-stage moving average filter are formed with a bit-stream processing circuit, such that the circuit structure is further simplified, and higher speed operation becomes possible.

Also, in accordance with the third embodiment of the invention, in the frequency measurement device that combines the short-gate time count method and the multiple-stage moving average filter that performs downsampling, the number of taps in the moving average filter and the sampling interval are adjusted, whereby the S/N is improved.

Also, according to the above-described embodiment examples (with the counter using the short-gate time count method), noise shaping works even after downsampling has been performed. Therefore, in contrast to other methods in which noise shaping does not work, a low-pass filter required before downsampling does not require high performance, such that the low-pass filter before downsampling can also be simplified (in other words, it is acceptable if the performance of the low-pass filter and components before and after downsampling as a whole is sufficient). Therefore, the structure of the low-pass filter can be simplified.

Also, sensors equipped with the frequency measurement device in accordance with any one of the embodiments of the invention are favorable, because the frequency measurement device is small in circuit scale and readily mountable, whereby size-reduction, higher accuracy, weight-reduction, power saving and lower cost of the apparatuses can be achieved.

What is claimed is:

1. A frequency measurement device comprising:
    a counter section that counts a supplied signal to be measured in a pulse stream at a predetermined time interval and outputs a stream of count values corresponding to the frequency of the signal to be measured; and
    a low-pass filter section that performs a filtering process on the stream of count values,
    the low-pass filter section including moving average filters in multiple stages, and an output of at least one moving average filter among the moving average filters in multiple stages is downsampled,
    sampling frequencies for acquiring data at the moving average filters in multiple stages decreasing at each of the stages of the moving average filters.

2. A frequency measurement device according to claim 1, the sampling frequencies decreasing at each of the stages of the moving average filters from the first stage to the last stage of the moving average filters.

3. A frequency measurement device according to claim 1, in downsampling between two consecutive ones of the moving average filters in forward and rear stages, at least one of the number of data delay taps in the moving average filter in the forward stage and the sampling frequency in the moving average filter in the rear stage being adjusted, such that a cumulative value of the data stream intermittently transmitted from the moving average filter in the forward stage to the moving average filter in the rear stage in a specified period becomes to be a constant value.

4. A frequency measurement device according to claim 1, the counter section and the moving average filter in the first stage in the low-pass filter section being formed from a circuit that processes a binary signal.

5. A frequency measurement device according to claim 1, the predetermined time being less than one second.

6. An apparatus equipped with the frequency measurement device recited in claim 1.

7. A frequency measurement method including continuously counting a supplied signal in a pulse stream to be measured at a predetermined time interval, and processing a stream of count values of the signal to be measured by a low pass filter to obtain an output signal corresponding to the frequency of the signal to be measure, the method comprising:
    setting sampling frequencies for acquiring data at moving average filters in multiple stages to decrease at each of the stages of the moving average filters from the first stage to the last stage of the moving average filters; and
    in downsampling between two consecutive ones of the moving average filters in forward and rear stages, adjusting at least one of the number of data delay taps in the moving average filter in the forward stage and the sampling frequency in the moving average filter in the rear stage, such that a cumulative value of the stream of data intermittently transmitted from the moving average filter in the forward stage to the moving average filter in the rear stage in a specified period becomes to be a constant value,
    sampling frequencies for acquiring data at the moving average filters in multiple stages decreasing at each of the stages of the moving average filters.

* * * * *